United States Patent [19]

Doria et al.

[11] 4,157,334

[45] * Jun. 5, 1979

[54] 6-CARBOXY-FLAVONE DERIVATIVES AND PROCESS FOR THEIR PREPARATION

[75] Inventors: Gianfederico Doria; Piernicola Giraldi; Francesco Lauria; Maria L. Corno, all of Milan; Piero Sberze, Varese; Marcello Tibolla, Canale d'Agordo, all of Italy

[73] Assignee: Carlo Erba S. p. A., Milan, Italy

[*] Notice: The portion of the term of this patent subsequent to Dec. 27, 1994, has been disclaimed.

[21] Appl. No.: 836,498

[22] Filed: Sep. 26, 1977

Related U.S. Application Data

[63] Continuation-in-part of Ser. No. 660,383, Feb. 23, 1976, Pat. No. 4,065,467, which is a continuation of Ser. No. 536,476, Dec. 26, 1974, abandoned.

[30] Foreign Application Priority Data

Oct. 21, 1976 [IT] Italy .............................. 28527 A/76

[51] Int. Cl.$^2$ ................... C07D 311/02; A61K 31/35
[52] U.S. Cl. .................................. 260/345.2; 424/283
[58] Field of Search ...................................... 260/345.2

[56] References Cited

U.S. PATENT DOCUMENTS

4,065,467 12/1977 Doria et al. ...................... 260/345.2

FOREIGN PATENT DOCUMENTS

823875 1/1975 Belgium .............................. 260/345.2

OTHER PUBLICATIONS

Shah et al., JACS, 77, 2223 (1955).
Shah et al., JCS, pp. 2663-2666 (1961).
Hsu et al., Chem. Abstract, 54, 4553g (1960).

*Primary Examiner*—Nicky Chan
*Attorney, Agent, or Firm*—Murray & Whisenhunt

[57] ABSTRACT

6-carboxy-flavone derivatives are disclosed, wherein the flavone derivative is substituted at the 2'-position with an alkoxy group, which may be substituted, and wherein the phenyl ring also carries an alkyl substituent.

The flavone derivatives exhibit anti-allergic activity and spasmolytic activity.

16 Claims, No Drawings

6-CARBOXY-FLAVONE DERIVATIVES AND PROCESS FOR THEIR PREPARATION

CROSS-REFERENCE TO PARENT APPLICATIONS

This application is a continuation-in-part of copending application Ser. No. 660,383 filed on Feb. 23, 1976, now U.S. Pat. No. 4,065,467, issued Dec. 27, 1977, which is, in turn, a continuation of application Ser. No. 536,476, filed on Dec. 26, 1974, now abandoned.

BACKGROUND OF THE INVENTION

The present invention is, as indicated hereinabove, a continuation-in-part application of copending application Ser. No. 660,383. That application discloses certain 6-carboxy flavone compounds which can carry one or more substituents on the phenyl ring thereof. While the generic formula of that application encompasses compounds wherein the phenyl ring carries an alkyl substituent and an alkoxy or alkenyloxy substituent, the only flavone compound specifically disclosed which has a phenyl ring carrying two substituents is the compound 6-carboxy-2', 6'-dimethoxyflavone, one of the compounds of Example 1 of application Ser. No. 660,383. The compounds which are claimed in the present application, however, unexpectedly exhibit greatly increased activity levels as compared to the compounds specifically disclosed in the copending application Ser. No. 660,383.

SUMMARY OF THE INVENTION

The present invention relates to 6-carboxy-flavone derivatives having the following general formula (I):

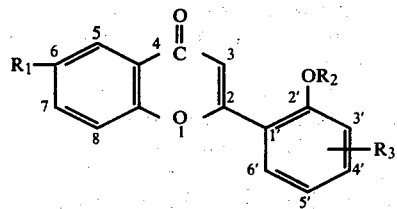

wherein
$R_1$ is
(a) carboxy or
(b) —$COOR_4$, wherein $R_4$ is $C_1$–$C_{12}$ or $C_3$–$C_4$ alkenyl;
$R_2$ is
(a') $C_1$–$C_6$ alkyl, which may be unsubstituted or substituted by $C_1$–$C_2$ alkoxy, or (b') $C_3$–$C_4$ alkenyl;
$R_3$ is $C_1$–$C_4$ alkyl,
to the salts thereof with pharmaceutically acceptable bases, to pharmaceutical compositions containing the compounds of formula (I) or the salts thereof and to a method for prevention and/or treatment of allergic conditions by administration of the compound of formula (I) or the salt thereof or of a pharmaceutical composition containing them.

DETAILED DESCRIPTION OF THE INVENTION

In the compounds of general formula (I) above, the alkyl, alkenyl, and alkoxy groups may be branched or straight chain.

Preferably, the compounds of the present invention are those compounds wherein $R_1$ is carboxy or carbalkoxy of 1 to 6 carbon atoms in the alkoxy group, and $R_2$ is a $C_1$–$C_6$ alkyl. More preferably, $R_2$ is a $C_1$–$C_4$ alkyl, most preferably methyl or isopropyl, or 2-ethoxy-ethyl. $R_4$ is most preferably $C_1$–$C_6$ alkyl, in particular ethyl, isopropyl, t-butyl or hexyl, and $R_3$, is preferably methyl or propyl. Preferably $R_1$ is carboxy. Preferably $R_3$ is in the 3', 4' or 5'-position on the phenyl ring, most preferably in the 5'-position.

Examples of pharmaceutically acceptable salts are either those with inorganic bases, such as sodium, potassium, calcium and aluminum hydroxides or with organic bases, such as lysine, triethylamine, triethanolamine, dibenzylamine, methylbenzylamine, di-(2-ethylhexyl)-amine, piperidine, N-ethyl-piperidine, N,N-diethylaminoethylamine, N-ethylmorpholine, β-phenethylamine, N-benzyl-β-phenethylamine, N-benzyl-N,N-dimethylamine and the other acceptable organic amines.

Examples of particularly preferred compounds of the invention are:
6-carboxy-2'-isopropoxy-3'-methyl-flavone;
6-carboxy-2'-isopropoxy-4'-methyl-flavone;
6-carboxy-2'-isopropoxy-5'-methyl-flavone;
6-carboxy-2'-isopropoxy-5'-ethyl-flavone;
6-carboxy-2'-isopropoxy-3'-propyl-flavone;
6-carboxy-2'-isopropoxy-5'-propyl-flavone;
6-carboxy-2'-isopropoxy-5'-isopropyl-flavone;
6-carboxy-2'-methoxy-3'-methyl-flavone;
6-carboxy-2'-methoxy-5'-methyl-flavone;
6-carboxy-2'-methoxy-3'-propyl-flavone;
6-carboxy-2'-(2''-ethoxy-ethoxy)-3'-methyl-flavone;
6-carboxy-2'-(2''-ethoxy-ethoxy)-5'-methyl-flavone,
as well as the pharmaceutically acceptable salts thereof, in particular the sodium salt, and the $C_1$–$C_6$ alkyl esters thereof, in particular the ethyl, isopropyl, tert-butyl and hexyl esters.

The compounds of the invention are prepared by cyclizing a compound of formula (II)

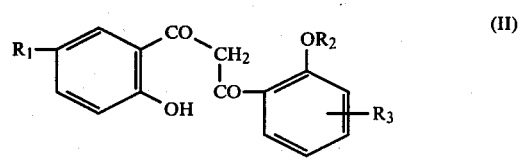

wherein
$R_1$, $R_2$ and $R_3$ are as defined above or a salt thereof and/or, if desired, converting a compound of general formula (I) into another compound of general formula (I) by known methods, and/or, if desired, converting a compound of general formula (I) into a pharmaceutically acceptable salt and/or, if desired, converting a salt into a free compound.

The cyclization of the compound of formula (II) is preferably performed in presence of acid catalysts, such as, for example, hydrochloric acid, hydroiodic acid, sulphuric acid, formic acid, at a temperature ranging perferably between 20° and 120° C. and in an inert solvent selected for instance from the group consisting of methanol, ethanol, dioxane, tetrahydrofuran, benzene, toluene, acetic acid and their mixtures.

A compound of general formula (I) may be converted, as hereabove stated, into another compound of general formula (I) by known methods. For example, a compound of formula (I) wherein $R_1$ is an esterified carboxy group, may be converted into a compound of formula (I) wherein R₁ is carboxy by basic hydrolysis, using, e.g. sodium or potassium hydroxide in a solvent such as a water or a lower aliphatic alcohol and operating at a temperature ranging from the room temperature to about 150° C.; the same reaction may be also carried out by treatment with lithium bromide in dimethylformamide at a temperature higher than 50° C.

A compound of general formula (I) wherein R is a carboxy group, may be converted into a compound of general formula (I) wherein R is an esterified carboxy group, for example, by reaction of the alkaline salt of the acid with the suitable alkyl or alkenyl halide, in an inert solvent such as acetone, dioxane, dimethylformamide, hexamethylphosphorotriamide at a temperature ranging from about 0° C. to about 100° C. Also the optional salification of the compounds of formula (I) as well as the optional conversion of a salt into a free acid, may be performed according to conventional methods. The compounds of formula (II) may be prepared by reacting a compound of formula (III)

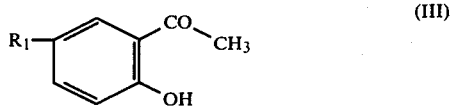

(III)

wherein
R₁ is as defined above with a compound of formula (IV)

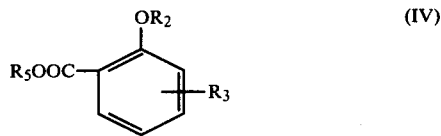

(IV)

wherein
R₂ and R₃ are as defined above and R₅ is aryl, preferably phenyl, or alkyl, preferably methyl or ethyl.

The reaction between the compound of formula (III) and the compound of formula (IV) is preferably effected in an organic solvent such as e.g. methanol, ethanol, dioxane and pyridine, in presence of a strong base, such as, for instance, sodium methoxide, sodium ethoxide, sodium hydride and at a temperature ranging between the room temperature and the reflux temperature.

An alternative method to prepare the compounds of formula (II) consists in reacting a compound of formula (III) with a compound of formula (V)

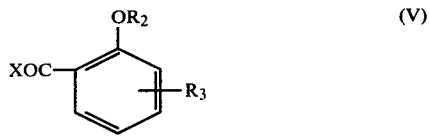

(V)

wherein
R₂ and R₃ are as defined above and X is halogen, preferably chlorine or bromine, by conventional methods, e.g. operating in an inert solvent such as benzene, toluene, dioxane at a temperature ranging from 0° C. to the reflux temperature, in the presence of a basic agent such as pyridine, triethylamine as acid acceptor, so obtaining a compound of formula (VI)

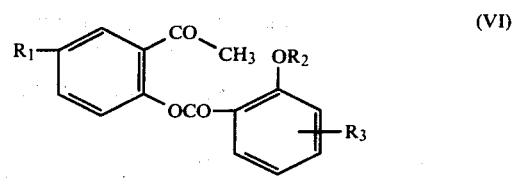

(VI)

wherein
R₁, R₂ and R₃ are as defined above and then submitting the compound of formula (VI) to a rearrangement to give the compound of formula (II); the rearrangement is carried out in an inert solvent, for example, pyridine, toluene, methyl-ethyl-ketone, isopropyl alcohol, in the presence of a strong base, e.g. sodium, sodium amide, potassium or sodium hydroxide, potassium or sodium carbonate, at a temperature ranging from the room temperature to the reflux temperature.

The compounds of formula (III) may be obtained from 4-acetoxy-benzoic acid or from suitable 4-acetoxy-benzoic esters by means of a Fries rearrangement, using AlCl₃ in the absence of solvents or in the presence of an inert solvent such as, preferably, tetrachloroethane, tetrachloroethylene, trichloroethylene, dichloroethane, at a temperature ranging from 20° C. to 180° C.

The compounds of formula (IV) and (V) are known compounds and may be prepared by conventional methods, starting from commercially available products, e.g. optionally substituted salicyclic acid or salicyclic esters.

The compounds of the invention own anti-allergic activity, as is shown by the fact that they are active in the passive cutaneous anaphylaxis (PCA) test in rats, according to Goose J. and Blair A.M.J.N. (Immunology, 16, 749, 1969).

They can be therefore used in prevention and treatment of e.g. bronchial asthma, allergic rhinitis, hay fever, urticaria and dermatosis. Furthermore, the compounds of the invention offer the important advantage of being highly active as anti-allergic agents also when orally administered, as is shown by the following Table, where the potency ratio of a compound of the invention is reported with respect to the compound 6-carboxy-2'-isopropoxy-flavone (K 10149), i.e. the most active flavone derivative among those described in the U.S. Application Ser. No. 536,476 filed on Dec. 26, 1974, now abandoned, corresponding to British Patent Specification No. 1,479,518.

To the anti-allergic activity of the compound K 10149 the conventional value 1 was given.

TABLE

| Compound | Potency ratio (K 10149=1) | Fiducial limits for P=0.95 |
|---|---|---|
| 6-carboxy-2'-isopropoxy-5'-methyl-flavone | 4.65 | (3.42–6.31) |

The anti-allergic activity was determined by the inhibition of the IgE-mediated PCA according to Goose J. and Blair A.M.J.N. (loc.cit.) using homocytotropic antibodies raised in rats following the method of Mota I., Immunology, 7, 681 (1964). The tested compounds were administered per os 15 minutes before the administration of the antigen at 3 or more dosage levels. At least 8 rats were used per each dose.

The potency ratios were calculated according to the method of Finney, D. J. (1952) Statistical Method in Biological Assay, C. Griffin London, page 118.

The compounds of the invention own also spasmolytic activity, for example the compound 6-carboxy-2'-isopropoxy-5'-methyl flavone has a spasmolytic activity on the guinea pig trachea (stimulated with acetylcholine) which is three times higher than that of K 10149. The compounds of the invention may be administered in a conventional manner, for instance, orally and parenterally at a daily dosage preferably of 0.25 to 15 mg/kg, or by inhalation, preferably at a daily dosage of 0.25 to 100 mg, preferably 0.5 to 25 mg, or by topical application.

The nature of the pharmaceutical compositions containing the compounds of this invention in association with pharmaceutically acceptable carriers or diluents will, of course, depend upon the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, or creams, or lotions for topical use.

Thus, for oral administration, the pharmaceutical compositions containing the compounds of this invention, are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone, disintegrating agents, such as, for instance, starches, alginic acid, alginates, sodium starch glycolate; effervescing mixtures; dyestuffs; sweeteners; wetting agents, such as, for instance, lecithin, polisorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin. The compounds of the invention may also be administered in the form of powders by means of a suitable insufflator device and in this case the fine particle sized powders of the active ingredient may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

EXAMPLES OF THE INVENTION

The following examples illustrate but do not limit the present invention. In these examples, all parts and percentages are by weight unless otherwise indicated.

EXAMPLE 1

Methyl 3-acetyl-4-hydroxy-benzoate (6 g) in dioxane (100 ml) was reacted with 2-isopropoxy-5-methyl-benzoyl chloride (10 g) in the presence of pyridine (10 ml) at room temperature for 16 hours. After dilution with water, the precipitate was extracted with ethyl acetate and the organic solution was washed with 5% NaHCO$_3$ and water and then evaporated to dryness to give methyl 3-acetyl-4-(2'-isopropoxy-5'-methyl-benzoyloxy)-benzoate (13 g, oil), which was dissolved in methyl-ethyl-ketone (200 ml) and treated with anhydrous potassium carbonate (22 g) under stirring at the reflux temperature for 4 hours.

After cooling the reaction mixture was diluted in ice-water and extracted with ethyl-acetate: the organic solution was washed with water and evaporated to dryness. The residue (12.7 g) was crystallized from methanol, so obtaining 8.1 g of (2-hydroxy-5-carbomethoxy-benzoyl)-(2-isopropoxy-5-methyl-benzoyl)-methane, m.p.=85°–86° C., which were refluxed for 15 minutes with 30 ml of 99% formic acid. After cooling and dilution with water the precipitate was extracted with chloroform and the organic solution was washed with water until neutral and then evaporated to dryness. The residue was crystallized from methanol to give 6.3 g of 6-carbomethoxy-2'-isopropoxy-5'-methyl-flavone, m.p.=149°–151° C., which were hydrolyzed with 1% solution of KOH in 95% ethanol (95 ml) at reflux temperature for 30 minutes. After cooling the reaction mixture was acidified with 23% HCl to pH=3 and the precipitate was filtered off and washed with ethanol and water so obtaining 5.9 g of 6-carboxy-2'-isopropoxy-5'-methyl-flavone, m.p.=209°–210° C.

By proceeding analogously, the following compounds were prepared:
6-carboxy-2'-isopropoxy-3'-methyl-flavone, m.p.=198°–200° C.;
6-carboxy-2'-isopropoxy-4'-methyl-flavone, m.p.=296°–298° C.;
6-carboxy-2'-isopropoxy-3'-propyl-flavone;
6-carboxy-2'-isopropoxy-5'-ethyl-flavone, m.p.=203°–205° C.;
6-carboxy-2'-isopropoxy-5'-propyl-flavone, m.p.=236°–237° C.;
6-carboxy-2'-isopropoxy-5'-isopropyl-flavone;
6-carboxy-2'-(2''-ethoxy-ethoxy)-3'-methyl-flavone;
6-carboxy-2'-(2''-ethoxy-ethoxy)-5'-methyl-flavone;
6-carboxy-2'-allyloxy-5'-methyl-flavone.

EXAMPLE 2

A solution of methyl 3-acetyl-4-hydroxy-benzoate (6 g) and methyl 2-methoxy-5-methyl-benzoate (12 g) in dioxane (40 ml) was slowly added under stirring at room temperature to a suspension of sodium hydride 50% (4.5 g) in dioxane (40 ml). The mixture was kept under stirring for 3 hours at 80° C., cooled, then diluted with petroleum ether (100 ml), and filtered. The collected precipitate was dissolved in water, acidified with acetic acid and extracted with ethyl-acetate. The organic phase was washed with potassium carbonate 5% and water, then evaporated to dryness and crystallized from ethanol to give (2-hydroxy-5-carbomethoxy-benzoyl)-(2-methoxy-5-methyl-benzoyl)-methane (7.9 g; m.p.=145°–147° C.), which was then refluxed for 15 minutes with 99% formic acid (28 ml). After cooling and dilution in water and filtration, the collected precipitate was crystallized from acetone to obtain 6-carbomethoxy-2'-methoxy-5'-methyl-flavone (6 g), m.p.=154°–156° C., which was hydrolyzed with a 1% solution of potassium hydroxide (100 ml) in 95% ethanol at reflux temperature for 30 minutes. The mixture was cooled, acidified with 23% HCl to pH=3, and the precipitate was filtered, washed with ethanol 95% and water so obtaining, after crystallization from ethanol, 6-carboxy-2'-methoxy-5'-methyl-flavone (5.3 g), m.p.=246°–247° C.

By proceeding analogously, the following compounds were obtained:
6-carboxy-2'-methoxy-3'-methyl-flavone;
6-carboxy-2'-methoxy-3'-propyl-flavone.

EXAMPLE 3

6-carboxy-2'-isopropoxy-5'-methyl-flavone (4.8 g) in dioxane (30 ml) was treated with thionyl chloride (4 ml) at the reflux temperature for 2 hours. After cooling, the reaction mixture was evaporated to dryness and reacted with an excess of anhydrous ethanol at 50° C. for 1 hour. The mixture was concentrated to a small volume and diluted with water so obtaining, by filtration, 6-carbethoxy-2'-isopropoxy-5'-methyl-flavone (4.7 g).

By proceeding analogously, the following compounds were prepared:
6-carbethoxy-2'-isopropoxy-3'-methyl-flavone;
6-carbethoxy-2'-isopropoxy-3'-propyl-flavone;
6-carbethoxy-2'-isopropoxy-4'-methyl-flavone;
6-carbethoxy-2'-isopropoxy-5'-propyl-flavone;
6-carbethoxy-2'-methoxy-5'-methyl-flavone;
6-carbethoxy-2'-(2''-ethoxy-ethoxy)-3'-methyl-flavone;
6-carbethoxy-2'-(2''-ethoxy-ethoxy)-5'-methyl-flavone.

EXAMPLE 4

By proceeding according to Example 3 and using the suitable aliphatic alcohols, the isopropyl ester, tert-butyl ester, hexyl ester and allyl ester of the following acids were prepared:
6-carboxy-2'-isopropoxy-3'-methyl-flavone;
6-carboxy-2'-isopropoxy-4'-methyl-flavone;
6-carboxy-2'-isopropoxy-5'-methyl-flavone;
6-carboxy-2'-isopropoxy-5'-propyl-flavone;
6-carboxy-2'-methoxy-5'-methyl-flavone;
6-carboxy-2'-(2''-ethoxy-ethoxy)-5'-methyl-flavone.

EXAMPLE 5

6-carboxy-2'-isopropoxy-5'-methyl-flavone (3.35 g) was treated with a hot aqueous solution containing NaHCO$_3$ (800 mg). The small undissolved portion of acid was filtered off and the clear solution was concentrated under vacuum nearly to dryness.

By treatment with acetone (250 ml) crystallization of the sodium salt of 6-carboxy-2'-isopropoxy-5'-methyl-flavone (3.15 g; m.p.>300° C.) was obtained. By proceeding analogously, the sodium salts of the following compounds were prepared:
6-carboxy-2'-isopropoxy-3'-methyl-flavone;
6-carboxy-2'-isopropoxy-4'-methyl-flavone;
6-carboxy-2'-isopropoxy-5'-propyl-flavone;
6-carboxy-2'-methoxy-5'-methyl-flavone;
6-carboxy-2'-(2''-ethoxy-ethoxy)-5'-methyl-flavone.

EXAMPLE 6

A mixture of 6-carboxy-2'-isopropoxy-5'-methyl-flavone (3.5 g) and N-methyl-N-benzyl-amine (1.6 g) was stirred at 120° C. for 30 minutes. After cooling, ethyl acetate (50 ml) was added and the mixture was left to crystallize under stirring.

After filtration and washing with ethyl acetate 4.35 g of N-methyl-N-benzylammonium salt of 6-carboxy-2'-isopropoxy-5'-methyl-flavone were obtained.

By proceeding analogously the N-methyl-N-benzylammonium salts of the following acids were prepared:
6-carboxy-2'-isopropoxy-3'-methyl-flavone;
6-carboxy-2'-isopropoxy-4'-methyl-flavone;
6-carboxy-2'-isopropoxy-5'-propyl-flavone;
6-carboxy-2'-methoxy-5'-methyl-flavone;
6-carboxy-2'-(2''-ethoxy-ethoxy)-5'-methyl-flavone.

EXAMPLE 7

Tablets, each weighing 150 mg and containing 50 mg of the active substances were manufactured as follows:

Composition (for 10,000 tablets)

6-carboxy-2'-isopropoxy-5'-methyl-flavone—500 g
lactose—710 g
corn starch—237.5 g
talc powder—37.5 g
magnesium stearate—15 g 6-carboxy-2'-isopropoxy-5'-methyl-flavone, lactose and a half of the corn starch were mixed; the mixture was then forced through a sieve of 0.5 mm openings. Corn starch (18 g) was suspended in warm water (180 ml). The resulting paste was used to granulate the powder mixture. The granules were dried, comminuted on a sieve of sieve size 1.4 mm, then the remaining quantity of starch, talc and magnesium stearate were added, carefully mixed, and processed into tablets using punches of 8 mm diameter.

EXAMPLE 8

Aerosol formulation 6-carboxy-2'-isopropoxy-5'-methyl-flavone—2%
ethanol—10%
lecithin—0.2%
mixture of dichlorodifluoromethane and dichlorotetrafluoroethane (70:30 mixture)—100%

What is claimed is:
1. A compound of the formula:

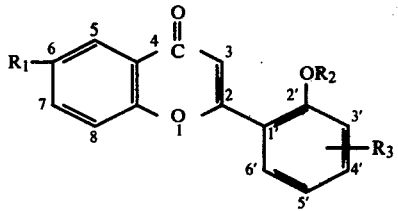 (I)

wherein
R₁ is
(a) carboxy or
(b) —COOR₄, wherein R₄ is $C_1$-$C_{12}$ alkyl or $C_3$-$C_4$ alkenyl;

R₂ is
(a') $C_1$-$C_6$ alkyl, which may be unsubstituted or substituted by $C_1$-$C_2$ alkoxy, or (b') $C_3$-$C_4$ alkenyl;

R₃ is $C_1$-$C_4$ alkyl; and the salts thereof with pharmaceutically acceptable bases.

2. Compound of claim 1, wherein R₁ is carboxy or carbalkoxy of 1 to 6 carbon atoms in the alkoxy group and R₂ is $C_1$-$C_6$ alkyl.

3. Compound of claim 2, wherein R₂ is $C_1$-$C_4$ alkyl and R₃ is methyl or propyl.

4. Compound of claim 3, wherein R₁ is carboxy.

5. 6-carboxy-2'-isopropoxy-5'-ethyl-flavone or a salt thereof, as claimed in claim 1.

6. 6-carboxy-2'-isopropoxy-3'-propyl-flavone or a salt thereof, as claimed in claim 1.

7. 6-carboxy-2'-isopropoxy-5'-propyl-flavone or a salt thereof, as claimed in claim 1.

8. 6-carboxy-2'-isopropoxy-5'-isopropyl-flavone or a salt thereof, as claimed in claim 1.

9. 6-carboxy-2'-methoxy-3'-methyl-flavone or a salt thereof, as claimed in claim 1.

10. 6-carboxy-2'-methoxy-5'-methyl-flavone or a salt thereof, as claimed in claim 1.

11. 6-carboxy-2'-methoxy-3'-propyl-flavone or a salt thereof, as claimed in claim 1.

12. 6-carboxy-2'-(2''-ethoxy-ethoxy)-3'-methylflavone or a salt thereof, as claimed in claim 1.

13. 6-carboxy-2'-(2''-ethoxy-ethoxy)-5'-methylflavone or a salt thereof, as claimed in claim 1.

14. 6-carboxy-2'-isopropoxy-3'-methyl-flavone or a salt thereof, as claimed in claim 1.

15. 6-carboxy-2'-isopropoxy-4'-methyl-flavone or a salt thereof, as claimed in claim 1.

16. 6-carboxy-2'-isopropoxy-5'-methyl-flavone or a salt thereof, as claimed in claim 1.

* * * * *